US012605045B2

(12) United States Patent
Sørensen

(10) Patent No.: US 12,605,045 B2
(45) Date of Patent: Apr. 21, 2026

(54) ENDOSCOPE AND A METHOD FOR MOULDING TRANSPARENT WINDOWS OF AN ENDOSCOPE

(71) Applicant: AMBU A/S, Ballerup (DK)

(72) Inventor: Morten Sørensen, Ballerup (DK)

(73) Assignee: AMBU A/S, Ballerup (DK)

( * ) Notice: Subject to any disclaimer, the term of this patent is extended or adjusted under 35 U.S.C. 154(b) by 398 days.

(21) Appl. No.: 18/033,992

(22) PCT Filed: Oct. 28, 2021

(86) PCT No.: PCT/EP2021/079985
§ 371 (c)(1),
(2) Date: Apr. 26, 2023

(87) PCT Pub. No.: WO2022/090394
PCT Pub. Date: May 5, 2022

(65) Prior Publication Data
US 2023/0397797 A1 Dec. 14, 2023

(30) Foreign Application Priority Data

Oct. 30, 2020 (EP) .................................... 20204977

(51) Int. Cl.
*A61B 1/00* (2006.01)
*B29C 45/16* (2006.01)

(52) U.S. Cl.
CPC ........ *A61B 1/00096* (2013.01); *A61B 1/0011* (2013.01); *B29C 45/16* (2013.01); *A61B 1/00045* (2013.01)

(58) Field of Classification Search
CPC .............. A61B 1/00096; A61B 1/0011; A61B 1/00045; B29C 45/16
See application file for complete search history.

(56) References Cited

U.S. PATENT DOCUMENTS

| | | | |
|---|---|---|---|
| 11,291,352 | B2 | 4/2022 | Vilhelmsen et al. |
| 2015/0005580 | A1 | 1/2015 | Petersen |

(Continued)

FOREIGN PATENT DOCUMENTS

| | | |
|---|---|---|
| EP | 3539449 A1 | 9/2019 |
| EP | 3718463 A1 | 10/2020 |

(Continued)

OTHER PUBLICATIONS

Extended European search report of European Application No. 20204977.1, 7 pgs., dated Apr. 21, 2023.

(Continued)

*Primary Examiner* — Mathieu D Vargot
(74) *Attorney, Agent, or Firm* — Faegre Drinker Biddle & Reath LLP

(57) ABSTRACT

Transparent windows (5, 6) of a housing of a tip part of an insertion endoscope are moulded by: Providing a moulding tool. Introducing in the moulding tool a first polymer material. Allowing the first polymer material to set to form a first housing part. Introducing in the moulding tool at least one second polymer material, where the second polymer material is different from the first polymer material and transparent. Allowing the second polymer material to set to form a combined housing component (4) with the first housing part. Removing the combined housing component (4) from the moulding tool. At least second polymer material is injected into the moulding tool via a plurality of inlets (Inl$_w$) to form a plurality of volumes of the second polymer material.

15 Claims, 5 Drawing Sheets

(56) References Cited

U.S. PATENT DOCUMENTS

| | | |
|---|---|---|
| 2017/0245734 A1 | 8/2017 | Kaneko |
| 2019/0282070 A1* | 9/2019 | Vilhelmsen .......... A61B 1/0011 |
| 2019/0282077 A1 | 9/2019 | Sørensen et al. |
| 2020/0060521 A1 | 2/2020 | Sørensen |
| 2021/0068642 A1 | 3/2021 | Sørensen |
| 2021/0127955 A1 | 5/2021 | Sørensen et al. |
| 2022/0133133 A1 | 5/2022 | Vilhelmsen et al. |
| 2022/0175224 A1 | 6/2022 | Sørensen et al. |

FOREIGN PATENT DOCUMENTS

| | | | |
|---|---|---|---|
| WO | 2010/066790 A1 | 6/2010 |
| WO | 2022263506 A1 | 12/2022 |

OTHER PUBLICATIONS

International Search Report of International Application No. PCT/EP2021/079985, 10 pgs., dated Jan. 19, 2022.

* cited by examiner

Display unit

ENDOSCOPE AND A METHOD FOR MOULDING TRANSPARENT WINDOWS OF AN ENDOSCOPE

CROSS-REFERENCE TO RELATED APPLICATIONS

This application is a National Phase entry under 35 U.S.C. § 371 of International Application No. PCT/EP2021/079985, filed Oct. 28, 2021, which claims the benefit of and priority from European Patent Application No. 20204977.1, filed Oct. 30, 2020; said applications are incorporated by reference herein in their entirety.

The present disclosure relates to an endoscope, more specifically to a tip housing for an endoscope and the manufacture thereof.

Insertion endoscopes normally comprise a proximal handle from which an insertion tube extends towards the distal end of the endoscope. At the distal end the insertion tube comprises an articulated bending section which the bending of which can be controlled by an operator using wheels and/or levers or the like at the handle. The articulated bending section comprises a number of articulated segments including a proximal segment for attachment to a tube forming the main body of the insertion tube, a number of intermediate segments, and a distal end segment comprising a tip part inter alia accommodating illumination and imaging electronics of the endoscope. In the endoscope, a working channel extends from an entry port in the handle through the insertion tube to an exit port in the distal end segment.

Figure 1:
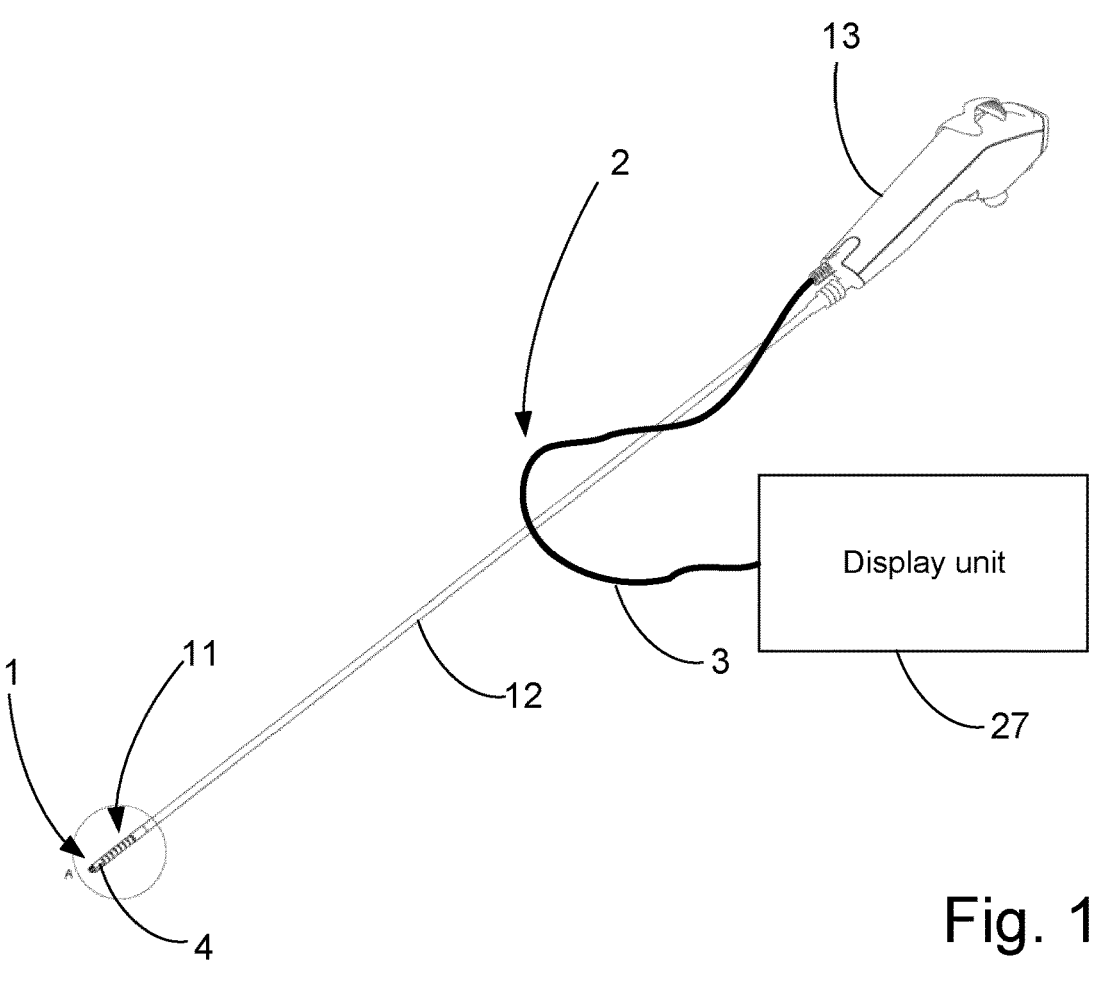

An example of such an insertion endoscope is the disposable endoscope known from EP3539449 incorporated herein by reference. As part of the distal segment this prior art endoscope comprises a tip housing as shown in FIG. 1 comprising an electronics compartment for accommodating inter alia said illumination and imaging electronics. Alongside the electronics compartment a working channel passage serving as a part of the working channel extends. The tip housing is manufactured as an integral item from plastic materials in a two-component two-stage insertion moulding process, comprising a transparent component for windows in front of the illumination devices and the imaging device. The other component preferably is opaque or dyed in order to absorb stray light from the illumination devices to enter directly into the imaging device.

When integrally moulding the transparent windows in the two-component two-stage insertion moulding process, it is important to make the optical properties as flawless as possible, i.e. keeping surfaces smooth, and keeping the transparency of the material within the window homogenous to avoid dispersion and refraction.

One problem in this respect is to control the flow of liquid transparent material into the mould cavity during the injection stage of the transparent material of the moulding where, due to the complex shape of the transparent window, homogenous filling of the mould cavity may provide difficulties.

Moreover, when as preferred the transparent material for the windows are injected in the second stage, there can be a tendency of the liquified material to dissolve minute quantities of the opaque material in the narrow passages between the different parts of the window. Although in minute quantities, this opaque material will also deteriorate the quality of the transparent material in the resulting windows.

Based on this it is the object to improve quality and the moulding process of transparent windows in an integrally formed tip housing of an endoscope.

According to a first aspect of the present disclosure this object is achieved by a method for moulding transparent windows of a housing of a tip part of an insertion endoscope, said method comprising providing a moulding tool, introducing in the moulding tool a first polymer material, allowing said first polymer material to set to form a first housing part, introducing in the moulding tool at least one second polymer material, where said second polymer material is different from said first polymer material, allowing said second polymer material to set to form a combined housing component with said first housing part, removing said combined housing component from said moulding tool, wherein one of said first and second polymer materials is s transparent polymer material and injected into said moulding tool via a plurality of inlets to form a plurality of volumes of said transparent polymer material.

According to a second aspect of the disclosure the object is achieved by an endoscope comprising a proximal handle, a distal tip part, and an insertion tube extending from the proximal handle towards the distal tip part, where said tip part comprises a tip housing integrally moulded from a first polymer material and a second polymer material different from the first polymer material, wherein said one of said first and second polymer materials is a transparent polymer material and forms a plurality of volumes separated from each other.

According to a third aspect of the disclosure the object is achieved by a system comprising a display unit and an endoscope according to the second aspect.

According to an embodiment of the first aspect of the disclosure said number of inlets in said plurality of inlets is equal to the number of volumes in said plurality of volumes. Thereby, the flow of liquified polymer material into each volume can be controlled, and the filling improved.

According to an embodiment of the disclosure, at least some of the volumes in said plurality of volumes differ from each other in size. By carefully choosing the sizes of the volumes, the flow of liquified polymer into the volume can further be controlled. Moreover, the selected shape and volume affects the other body part thereby allowing it to be shaped for better filling with the other liquified polymer material.

According to an embodiment of the disclosure, said volumes of said transparent polymer material are separate from each other. Separating the volumes entirely from each other allows good control over the stay light, e.g. preventing undesired stray light from the slight sources to enter the image receptor without first leaving the endoscope and being reflected from the exterior.

According to an embodiment of the disclosure, said number of volumes is three. Experience shows that three windows suffice, i.e. one for imaging and two for illumination, and keeping the number down simplifies the mould as well as the moulding process.

According to an embodiment of the disclosure, one of said first or polymer material is opaque. This prevents stray light between the transparent parts.

Figure 2:
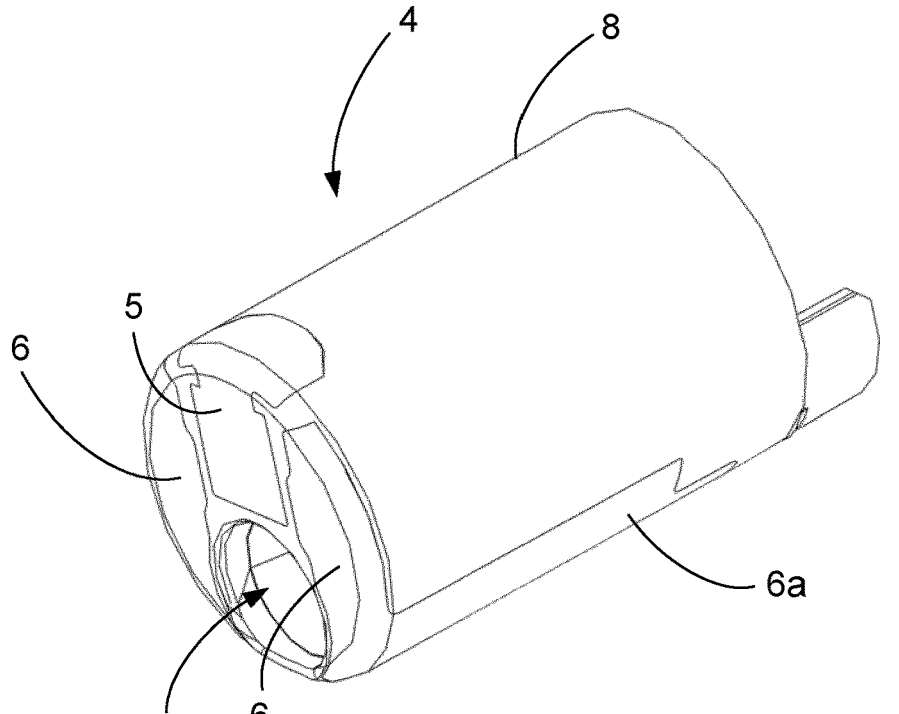
Figure 3:
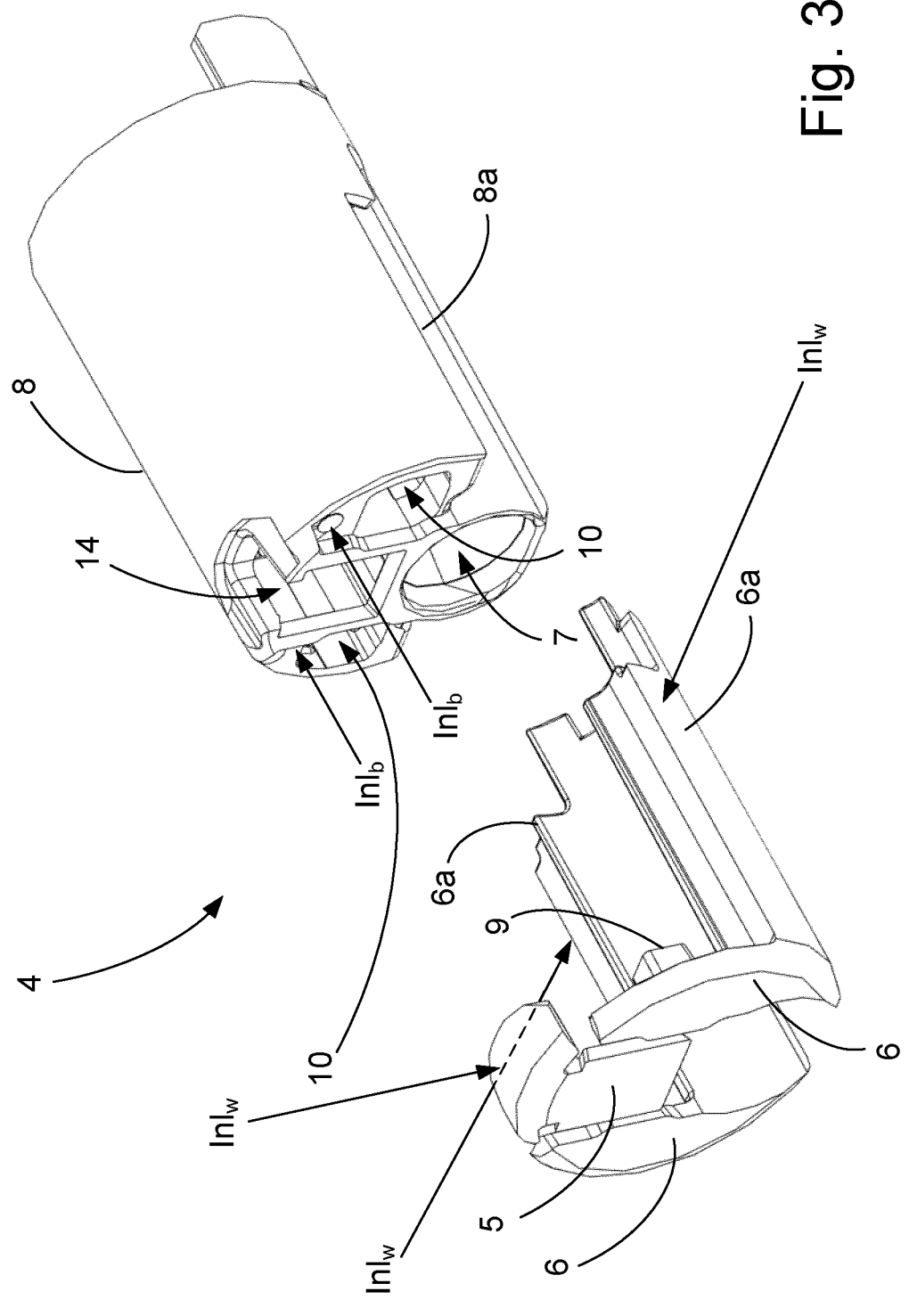
Figure 4:
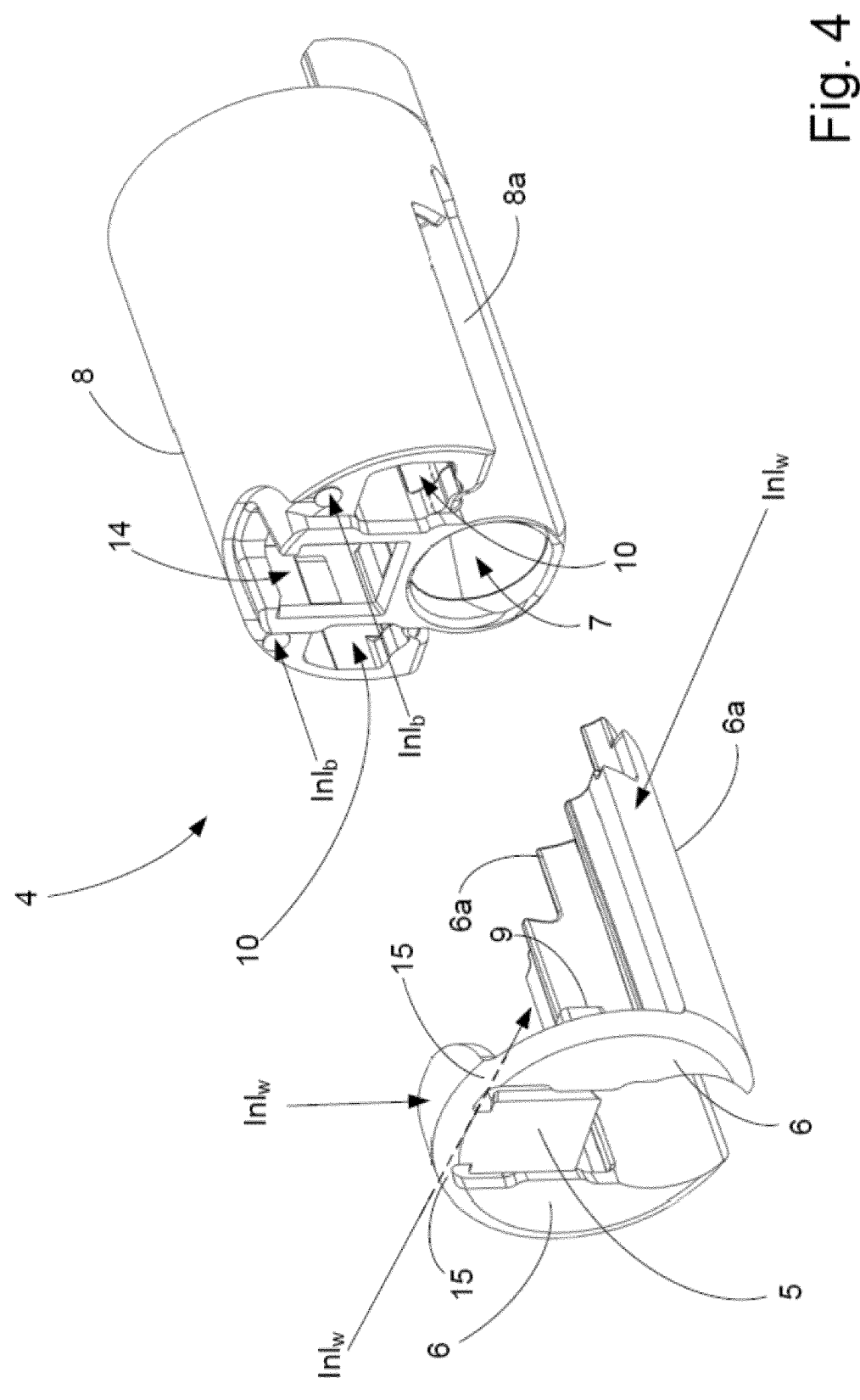
Figure 5A:
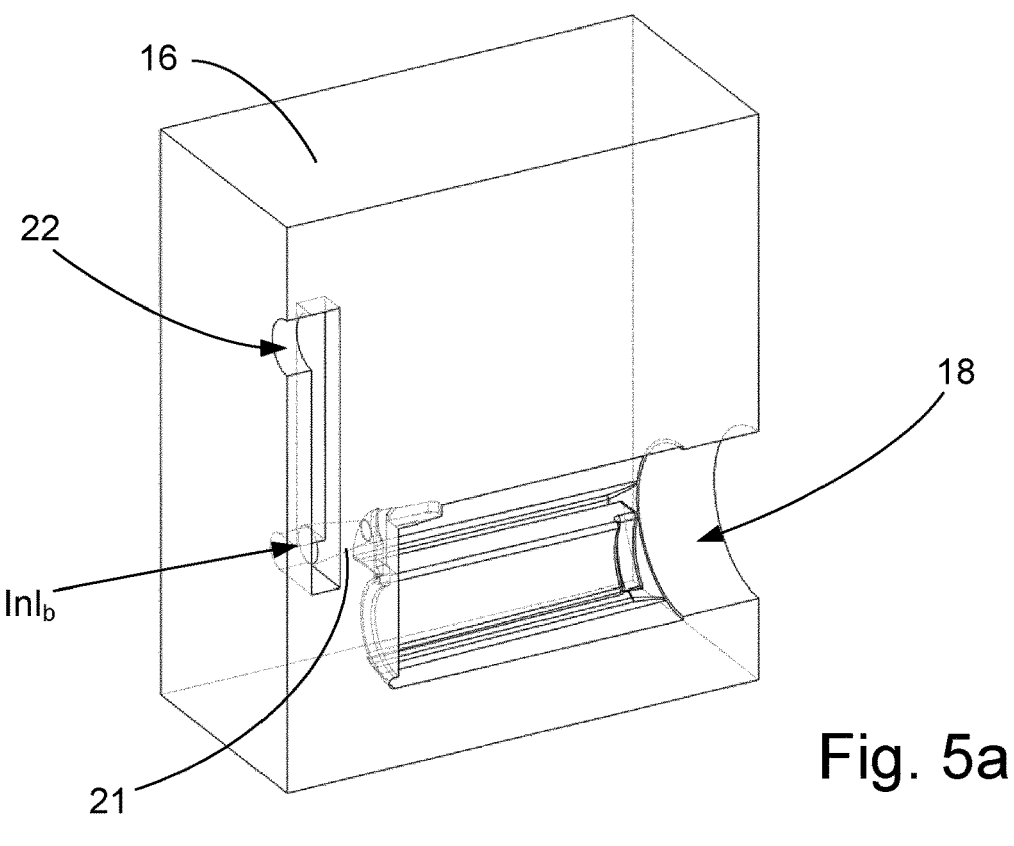
Figure 5B:
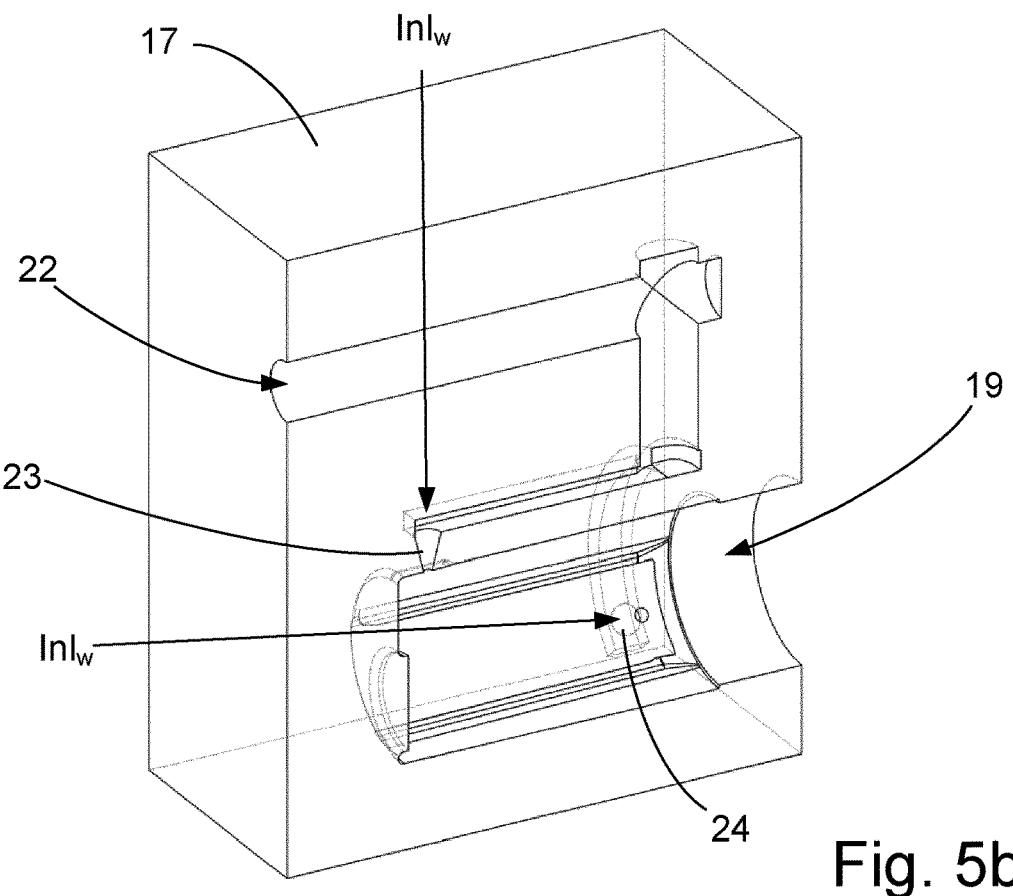
Figure 6C:
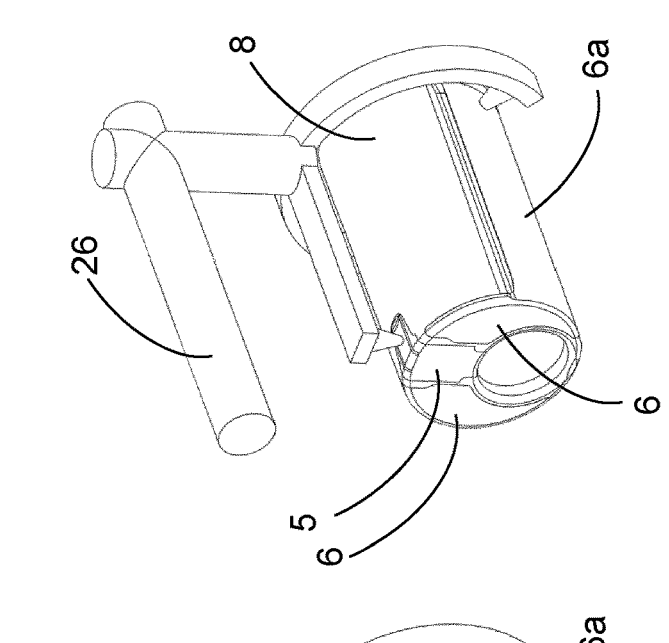
Figure 6B:
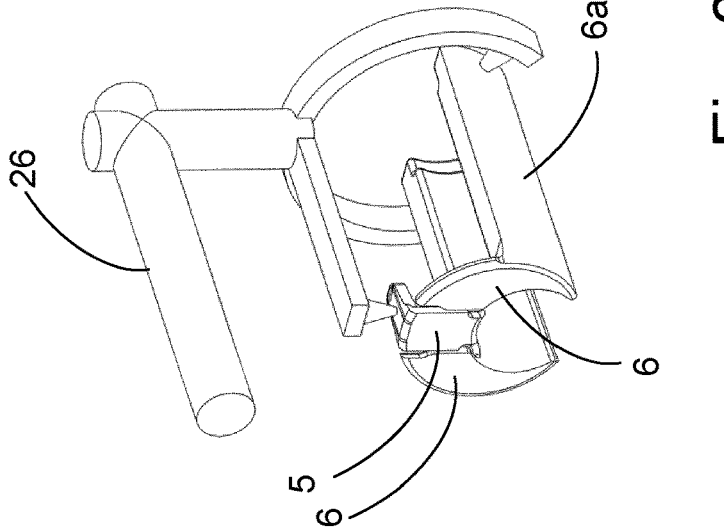
Figure 6A:
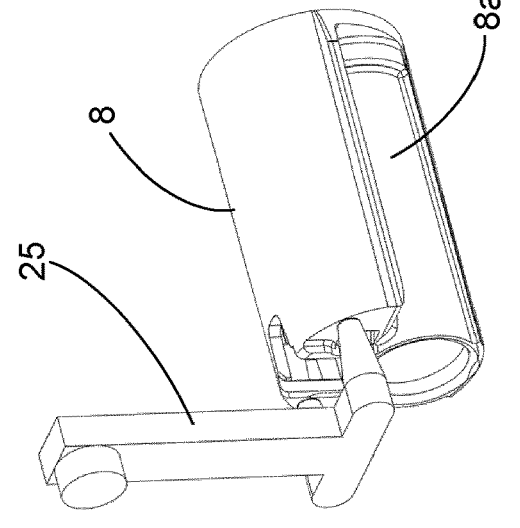

The disclosure will now be made in greater detail based on nonlimiting exemplary embodiments and with reference to the drawings, on which:

FIG. 1 shows a system comprising a display unit and an endoscope according to the disclosure, FIG. 2 shows the housing of the tip part of the endoscope of the disclosure, FIG. 3 shows an exploded view of the housing of FIG. 2 illustrating the manufacture thereof, FIG. 4 shows an exploded view of an alternative embodiment of the housing of the tip part, FIG. 5a-5c show the moulded components of the housing of a further alternative embodiment before the inlet residuals are removed, and FIGS. 6a and 6b show the concave mould parts for moulding of the further alternative embodiment.

Turning first to FIG. 1, a system comprising an endoscope 2, a disposable or single-use endoscope and a reusable display unit 27 to which the endoscope 2 is connected, is shown. The connection may be any suitable supply or communication means such as a cable 3.

The proximal end of the endoscope 2 comprises a handle 13 from which an insertion tube 12 extends towards an articulated bending section 11 at the distal end of the endoscope 2. The bending section 11 is connected to a distal tip part 1 comprising a housing 4, accommodating inter alia the illumination and image reception means of the endoscope, such as LEDs and an electronic image sensor (not shown).

The housing 4 is shown in greater detail in FIG. 2. As will be explained below, the housing 4 is manufactured by to-stage two-component injection moulding from suitable polymer materials. Accordingly, it comprises a first transparent polymer material from which windows 5, 6 are made. The windows 5, 6 may comprise a central window 5 located above the working channel 7 in the orientation of the illustration, and two lateral windows 6 on either side of the working channel 7. As can be seen the two lateral windows 6, comprise parts 6a which extend quite a substantial way along the length of the second housing part 8. The second housing part 8 is preferably made from a second polymer, different from the first polymer material, e.g. by being opaque, coloured or the like. Being opaque is preferred as it reduces stray light between the windows 6 in front of the illumination sources, such as LEDs, to the central window 5 in front of the image receptor, such as a camera or an electronic image sensor.

Turning now to FIG. 3 an exploded view of the housing of FIG. 2 is shown. It can be seen that the working channel 7 is provided exclusively in the second housing part 8. It can also be seen that the transparent windows 6, may comprise light guides 9 for guiding light from the LEDs accommodated in compartments 10 provided in the second housing part 8 to the exterior in front of the tip part 1. Also, in the second housing part 8, a compartment 14 for the imaging electronics behind the central window 5 is provided.

The housing 4 is preferably manufactured by two-stage two-component injection moulding. Similar to the description of EP3539449, incorporated herein by reference, the second housing part is first moulded by injection moulding in a first mould configuration where one mould part has a concave shape complementary to the outer shape of the resulting housing part 8, and a core or mandrel having a convex shape complementary to the internal shape of the resulting housing part 8. For this the liquified first polymer material is injected into the mould via an inlet arranged at a location indicated by the arrows $Inl_b$. In the illustrated example there are two inlets. A single inlet as well as other locations and more inlets are of course not excluded, as this depends on the actual design of the housing part 8. After injection the injected first polymer material sets or solidifies. The housing part 8 can then be taken to a second mould configuration by changing the concave form part to one having an outer shape which together with the mandrel and the solidified housing part provides the shapes of the window parts 5, 6. As can be seen from FIG. 3 the design of the housing part 8 is so that a plurality in casu three distinct, i.e. separate, volumes for the windows 5, 6 occur in the second mould. Each of these three separate volumes are filled via an inlet dedicated to the specific volume, e.g. located as indicated with the arrows $Inl_w$. That is to say, there is a plurality of inlets to the second mould configuration, where the number of inlets match the number of volumes in the plurality of volumes. Some volumes could have more than one inlet so that the number of inlets in the plurality of inlets is larger than the number of volumes. When the second polymer material has set or solidified, the two polymer materials are fused together and an integral housing 4 comprising both transparent windows 5, 6 made of the second transparent polymer material and an opaque housing part 8 made of the first polymer material is provided. The integral housing 4 may then joined to the bending section 11, fitted with electronics, sealed. Thus, an endoscope 2, in particular a disposable or single-use endoscope, using it can be provided.

As can be seen, the volumes of the transparent windows 6 for the illumination devices extend backwardly in two lateral wings 6a from the actual window and lightguides 9, i.e. to locations where illumination is not needed. This allows the inlet to be placed far behind the critical zones of the actual window 6 and lightguide 9 where distortions from the turbulent flow of liquified transparent material could remain in the set or solidified window material. These backward parts of the volume are moreover quite large as compared to the actual windows and so as to further reduce turbulence before the material reaches the critical zones. Furthermore, these lateral wings 6a distribute the material necessary for the housing 4 between the transparent window parts 5, 6 and the opaque housing part 8 in an advantageous way. That is to say, complementary recesses 8a are provided in the opaque housing part 8. These recesses 8a reduce the material thickness of some of the features of the opaque housing parts close to the inlets indicated with the arrows $Inl_w$. This allows a more uniform injection as there are no large easily accessible volumes acting like sinks for the liquified transparent polymer material and preventing it from entering properly into the narrower volumes and passages and propagating towards the other end of the mould. Furthermore, if such volumes were to be filled first, the liquified polymer material would have a tendency to set in these volumes before the flow resistance allows the liquified polymer material allows material to be pressed into the narrower passages. The opposite is not the case for the wings 6a that rather act like large conduits funneling the liquified transparent polymer material towards the narrower features at the actual window 6 and the light guides 9.

Turning now to FIGS. 5a and 5b cross-sections first and second concave mould parts 16, 17 for the two stages of injection moulding are schematically shown. Outlines of otherwise invisible parts are shown in dotted lined for illustration purposes. The mould parts 16, 17 are here referred to as concave as they comprise an internal mould cavity 18, 19, respectively. A complementary convex mould part which would close the moulds 16, 17 on the righthand side thereof in FIGS. 5a and 5b is not shown as it does not comprise inlets and therefore in this context can be considered per se know by the person skilled in the art. It is referred to as convex as it would comprise a central mandrel extending into the respective moulds cavities 18, 19 and serving to hold the second housing part 8 while, after the first stage of the moulding process, the first mould part 16 is replaced with the second mould part 17, for the subsequent moulding of the transparent windows 5, 6 including the light guides 9 in the second moulding stage of the process.

The first mould 16 comprises a supply channel 22 for liquified polymer material. The supply channel 22 splits to form two inlet passages 21 of which only one is visible in the cross-section of FIG. 5*a* to the mould cavity 18. Once the liquified polymer material has set, the resulting shape of the second housing part 8 will be as shown in FIG. 6*a*. The residual material 25, i.e. sprue runners and from the supply channel 22 and passages 21 to the inlets, will break off from the second housing part 8 when the second housing part 8 is extracted from the mould cavity 18, and the mandrel with the second housing part 8 placed in the second mould cavity 19.

The second mould 17 similarly comprises a supply channel 22 for liquified polymer. This supply channel 22 splits in three to provide separate inlet passages 23, 24 for the window 5, 6 including the wings 6*b* and possibly light guides 9. Here again, only one of the inlet passages 24 is visible in the cross-section of FIG. 5*b*, but the resulting shape of the window 6 including the wings 6*b* and possibly light guides 9, will be connected via the residual material 26 and the passages 23, 24 to the inlets will be as shown in FIG. 6*b*. FIG. 6*b*, however, is just illustrative and the resulting item after the second mould stage will be as illustrated in FIG. 6*c*, where the housing 8 of the second material is fused together with the windows 5, 6 including the wings 6*b* and possibly light guides 9 to form an integrally moulded body. When removed from the mould the residual material, i.e. sprue and runners, is broken off leaving inlet marks only at sites where optical properties of the transparent material is not jeopardized.

The other embodiments described would be moulded in a corresponding manner, irrespective of whether the windows are fully separated distinct windows or interconnected with narrow passages.

Although, it is currently preferred to mould the transparent material as the second material in the second stage the skilled person will know that it is equally possible to mould the transparent material as the first material in a concave part of the mould and then changing the mould configuration by insertion of a different convex mould part into to the concave part of the core.

Furthermore, although it is currently preferred to mould a plurality of entirely distinct or separated transparent windows 5, 6, it is not excluded that they may be interconnected by narrow bridges 15 as illustrated in FIG. 4, e.g. in order to secure their mutual position in the mould if the transparent material is moulded in the first stage of the two-stage two-component injection moulding process. As long as each of the interconnected volumes 5, 6 is filled through it's own dedicated inlet $Inl_w$, the problems of dissolving opaque material in the passages, and deterioration of the window quality is still avoided as the material does not pass through these passages 15. For this it may be relevant to delay some of the flow to some of the volumes 5, 6, e.g. by extending the flow path through the channels to the inlets, to ensure that the individual flows meet up in the passages. Such a delay may also be an option to prevent dislocation or deformation of the item or items moulded in the first stage, even if the volumes moulded in the second stage are entirely separate.

What is claimed is:

1. A method for moulding a housing of a tip part of an insertion endoscope, said method comprising:

molding, from an opaque polymer material, an opaque housing part comprising a circumferential wall including a first longitudinal recess forming a first recess volume and a second longitudinal recess forming a second recess volume, introducing into a moulding tool, through a plurality of inlets in the moulding tool and with the opaque housing part in the moulding tool, a transparent polymer material to form three volumes of the transparent polymer material, the three volumes being distinct and separated from each other by portions of the opaque polymer material, a first of the three volumes forming a first lateral window and a first longitudinal wing, a second of the three volumes forming a second lateral window and a second longitudinal wing, the first longitudinal wing formed in the first recess volume and the second longitudinal wing formed in the second recess volume, and a third of the three volumes forming a central window disposed between the first lateral window and the second lateral window, allowing said transparent polymer material to fuse with the opaque housing part and set to form a combined housing component, and removing said combined housing component from said moulding tool.

2. The method of claim 1, wherein said plurality of inlets consists of three inlets.

3. The method of claim 1, wherein the first of the three volumes and the second of the three volumes are larger than the third of the three volumes.

4. An endoscope comprising:

a proximal handle, a distal tip part, and an insertion tube extending from the proximal handle towards the distal tip part, the distal tip part including a housing comprising:

an opaque housing part comprising a circumferential wall including a first longitudinal recess forming a first recess volume and a second longitudinal recess forming a second recess volume;

a first portion of a transparent polymer material, the first portion forming a first lateral window and a first longitudinal wing received in and fused to the first longitudinal recess;

a second portion of the transparent polymer material, the second portion forming a second lateral window and a second longitudinal wing received in and fused to the second longitudinal recess; and a third portion of the transparent polymer material, the third portion forming a central window disposed between the first lateral window and the second lateral window, wherein the first portion, the second portion, and the third portion are distinct and separated from each other by portions of the opaque polymer material, and wherein the first portion, the second portion, the third portion and the opaque housing part form a combined housing component.

5. The endoscope of claim 4, wherein the first portion and the second portion are larger than the third portion.

6. A system comprising:

a display unit; and the endoscope of claim 4.

7. The method of claim 1, wherein the first of the three volumes extends proximally into a cavity formed by the opaque housing part to form a first lightguide, and wherein the second of the three volumes extends proximally into the cavity formed by the opaque housing part to form a second lightguide.

8. The method of claim 1, wherein the first longitudinal wing and the second longitudinal wing extend proximally from the central window past a midpoint of a length of the opaque housing part.

9. The method of claim 1, wherein the moulding tool includes a first concave mould tool and a second concave mould tool, and wherein the second concave mould tool includes the plurality of inlets.

10. The method of claim 9, the method further comprising substituting the first concave mould tool with the second concave mould tool after the opaque polymer material sets and before introducing the transparent polymer material.

11. The method of claim 1, wherein at least two of the plurality of inlets comprise openings to the first recess volume and to the second recess volume, and wherein the method comprises introducing, through said openings, all of the transparent polymer material forming the first of the three volumes and the second of the three volumes.

12. The method of claim 11, wherein one of the plurality of inlets comprises an opening to the third recess volume, and wherein the method comprises introducing, through said opening, some of the transparent polymer material to form the third of the three volumes.

13. The method of claim 12, wherein the transparent polymer material introduced to the first recess volume and to the second recess volume does not flow to the third recess volume.

14. The method of claim 1, wherein the central window, the first lateral window, and the second lateral window lie perpendicularly to a longitudinal axis of the combined housing component.

15. The endoscope of claim 4, wherein the central window, the first lateral window, and the second lateral window lie perpendicularly to a longitudinal axis of the combined housing component.

* * * * *